United States Patent
Zhang

(10) Patent No.: US 9,572,827 B2
(45) Date of Patent: Feb. 21, 2017

(54) PHARMACEUTICAL COMPOSITION FOR TREATING DEPRESSION AND METHOD FOR PREPARATION THEREOF

(71) Applicants: Beijing Wonner Biotech, Ltd. Co., Beijing (CN); Zuoguang Zhang, Beijing (CN); Yu-Fen Chi, Yonghe, Taipei County (TW)

(72) Inventor: Zuoguang Zhang, Beijing (CN)

(73) Assignees: Beijing Wonner Biotech. Ltd. Co., Beijing (CN); Zuoguang Zhang, Beijing (CN); Yu-Fen Chi, Yonghe (TW)

( * ) Notice: Subject to any disclaimer, the term of this patent is extended or adjusted under 35 U.S.C. 154(b) by 158 days.

(21) Appl. No.: 14/076,861

(22) Filed: Nov. 11, 2013

(65) Prior Publication Data

US 2014/0065125 A1   Mar. 6, 2014

Related U.S. Application Data

(63) Continuation of application No. 11/909,087, filed as application No. PCT/CN2005/001796 on Oct. 31, 2005, now abandoned.

(30) Foreign Application Priority Data

Mar. 25, 2005   (CN) .......................... 2005 1 0058987

(51) Int. Cl.
| | | |
|---|---|---|
| *A61K 36/258* | (2006.01) | |
| *A61K 36/185* | (2006.01) | |
| *A61K 31/704* | (2006.01) | |
| *A61K 36/484* | (2006.01) | |
| *A61K 36/725* | (2006.01) | |
| *A61K 31/7076* | (2006.01) | |
| *A61K 38/51* | (2006.01) | |

(52) U.S. Cl.
CPC ......... *A61K 31/704* (2013.01); *A61K 31/7076* (2013.01); *A61K 36/258* (2013.01); *A61K 36/484* (2013.01); *A61K 36/725* (2013.01); *A61K 38/51* (2013.01)

(58) Field of Classification Search
None
See application file for complete search history.

(56) References Cited

U.S. PATENT DOCUMENTS

| | | | |
|---|---|---|---|
| 5,589,182 A | * | 12/1996 | Tashiro ................ A61K 36/074 424/195.18 |
| 6,083,932 A | | 7/2000 | Pang et al. |
| 6,395,311 B2 | | 5/2002 | Jia |
| 2004/0137087 A1 | | 7/2004 | Shan et al. |
| 2005/0079234 A1 | | 4/2005 | Chiang |
| 2010/0310682 A1 | | 12/2010 | Zhang |
| 2013/0040903 A1 | | 2/2013 | Zhang |

FOREIGN PATENT DOCUMENTS

| | | | |
|---|---|---|---|
| CN | 1194100 A | | 9/1998 |
| CN | 1308959 A | | 8/2001 |
| CN | 1312089 A | | 9/2001 |
| CN | 1416881 A | * | 5/2003 |
| CN | 1611232 A | | 5/2005 |
| EP | 2 221 058 A1 | | 8/2010 |
| JP | 2005 278604 A | | 10/2005 |
| JP | 2011 504886 A | | 2/2011 |
| JP | 2011 504887 A | | 2/2011 |
| KR | 10-2010-0110786 A | | 10/2010 |
| RU | 02000800 C1 | | 10/1993 |

OTHER PUBLICATIONS

Database TCM [ Online] SIPO; "A medicine, Energy Pleasing and the depressed vital energy dispersing prescription, for the treatment of psychosis/A pharmaceutical composition for the treatment of psychosis," XP002471316; Aug. 22, 2001.
Database WPI Week 200572, Thomson Scientific, London, GB, XP002487255; Oct. 13, 2005.

* cited by examiner

Primary Examiner — Chris R Tate
Assistant Examiner — Randall Winston
(74) Attorney, Agent, or Firm — Volpe and Koenig, P.C.

(57) ABSTRACT

A pharmaceutical composition for treating depression and method for preparation thereof is provided. The pharmaceutical composition includes Radix *Ginseng*, Radix *Glycyrrhizae*, and/or their aqueous or alcoholic extract. Fructus *Jujubae* or their aqueous or alcoholic extract can also be included in the pharmaceutical composition.

8 Claims, 3 Drawing Sheets

PHARMACEUTICAL COMPOSITION FOR TREATING DEPRESSION AND METHOD FOR PREPARATION THEREOF

This application is a continuation of U.S. patent application Ser. No. 11/909,087, filed Sep. 19, 2007, which was a national stage application of International Application PCT/CN05/01796, filed Oct. 31, 2005, which claimed the benefit of CN200510058987.3, filed Mar. 25, 2005, all of which are incorporated herein by reference as if fully set forth.

FIELD OF THE INVENTION

The present invention relates to a pharmaceutical composition. In particular, the present invention relates to a pharmaceutical composition for treating depression as the main effect. The present invention further relates to a preparation method of the pharmaceutical composition for treating depression as the main goal.

BACKGROUND OF THE INVENTION

Depression is a common disease. According to statistics, about 25% females in the global population had been experiencing depression in their lives, and about 10% males had been experiencing depression (referring to *Modern Psychology* written by Ch'un-Hsing Chang). World Health Organization (WHO) published, "The incidence of depression in the world is about 11%. At present, about 340 million psychological depressed patients are in the world, and the number is increased. The investigation is found that the depression will be increased to be the number two common disease in the world from now on to 20 years later."

At present, anti-depression pharmaceuticals in the domestic and overseas markets consist mainly selective serotonin reuptake inhibitors (SSRIs), such as Prozac (fluoxetine hydrochloride), Paxil (Paroxetine or paroxetine hydrochloride) and Zoloft (sertraline hydrochloride), etc. These pharmaceuticals function by increasing the component and the content of serotonin in the human body to decrease and release the symptoms of depression. This kind of pharmaceuticals all have side effects of different levels. The research is published that these pharmaceuticals have the ability to correct chemical imbalance in the human body, but more often than not, they are still unable to calm the patients. In recent years, whether the depression pharmaceuticals, such as Prozac, are harmful had became a serious social problem, whereas Paxil was even found to be harmful in 1996. Paxil has been recalled continually from the market since 2001. In June 2004, the New York State Attorney General accused GlaxoSmithKline Company of the Great British of beguilingly concealing the research report of the linkage between Paxil and "increased risk of suicidal behavior and tendencies in adolescents." In light of the current situation, the search for a new generation of pharmaceuticals with less side effects and more pronounced/potent anti-depression qualities has become the center of attention of the entire pharmaceutical world.

It is therefore attempted by the applicant to deal with the above situation encountered in the prior art.

SUMMARY OF THE INVENTION

In order to overcome the insufficiency of the modern technology, the purpose of the present invention provides a herbal pharmaceutical composition for anti-depression as the main effect. It can be used as pharmaceuticals or health food for improving the depression.

According to one aspect of the present invention, a pharmaceutical composition for treating depression is provided. The pharmaceutical composition at least comprises one of the following compositions of raw materials: (A) 4~18 parts by weight of a *ginseng* and 3~14 parts by weight of a liquorice; (B) a *ginseng* extract extracted from 4~18 parts by weight of the *ginseng* and a liquorice extract extracted from 3~14 parts by weight of the liquorice; (C) 4~18 parts by weight of the *ginseng* and the liquorice extract extracted from 3~14 parts by weight of the liquorice; and (D) a *ginseng* extract extracted from 4~18 parts by weight of the *ginseng* and 3~14 parts by weight of the liquorice.

Preferably, the pharmaceutical composition further comprises one of 3~14 parts by weight of a jujuba and a jujuba extract extracted from 3~14 parts by weight of the jujuba, wherein the jujuba extract is one of a jujuba water extract and a jujuba ethanol extract.

Preferably, the pharmaceutical composition further comprises one of 4~8 parts by weight of a jujuba and a jujuba extract extracted from 4~8 parts by weight of the jujuba.

Preferably, the composition (A) of the raw materials is formed by 7~11 parts by weight of the *ginseng* and 4~8 parts by weight of the liquorice.

Preferably, the *ginseng* extract of the composition (B) of the raw materials is extracted from 7~11 parts by weight of the *ginseng* and the liquorice extract thereof is extracted from 4~8 parts by weight of the liquorice.

The pharmaceutical composition may comprise a pharmacologically acceptable additive, or none at all.

Preferably, wherein the pharmaceutical composition is processed into one selected from a group of a powder, a capsule, a tablet, and a pill.

Preferably, the *ginseng* extract is one of a *ginseng* water extract and a *ginseng* ethanol extract, and the liquorice extract is one of a liquorice water extract and a liquorice ethanol extract.

According to another aspect of the present invention, a pharmaceutical composition for treating the depression is provided. The pharmaceutical composition comprises: a *ginseng* extract extracted from 3A~10A parts by weight of a *ginseng* and having B % content of a ginsenoside, wherein a multiplication product of B and A is 20~40, and A is ranged between 0.2 and 40; and 0.2C~0.8C part by weight of a glycyrrhizically related acid having D % purity, wherein a multiplication product of D and C is 80~98, and C is ranged between 0.8 and 98.

Preferably, the *ginseng* is one of a *ginseng* water extract and a *ginseng* ethanol extract, and the glycyrrhizically related acid is one of a glycyrrhizic acid and a glycyrrhetic acid.

Preferably, the *ginseng* ethanol extract comprises 20~40% content of the ginsenoside, and the purity of the glycyrrhizically related acid is 80~98%.

Preferably, the pharmaceutical composition further comprises a jujuba extract extracted from 0.05E~0.2E part by weight of a jujuba and having F % content of a jujuba cyclic adenosine monophosphate (cAMP), wherein a multiplication product of F and E is 0.5~3, E is ranged between 0.005 and 3, and the jujuba extract is one of a jujuba water extract and a jujuba ethanol extract.

Preferably, the jujuba ethanol extract comprises 0.5~3% content of the jujuba cAMP.

Preferably, the *ginseng* extract is an ethanol extract extracted from 4~6 parts by weight of the *ginseng* and has 25~35% content of ginsenoside, the glycyrrhizically related acid is 0.3~0.5 part by weight of a glycyrrhetic acid having 85~95% purity, and the pharmaceutical composition further comprises a jujuba ethanol extract extracted from 0.08~0.12 part by weight of a jujuba and having 0.8~1.2% purity of a jujuba cAMP.

The pharmaceutical composition may comprise a pharmacologically acceptable additive, or none at all.

Preferably, the pharmaceutical composition is processed into one selected from a group consisting of a powder, a capsule, a tablet, and a pill.

According to another aspect of the present invention, a preparation method of a pharmaceutical composition is provided. The preparation method comprises steps of: (1) decocting 4~18 parts by weight of a *ginseng* in 60~77% concentration of an ethanol solution to obtain a first extract; (2) decocting 4~18 parts by weight of a liquorice in a water to obtain a second extract; and (3) mixing and sifting the first extract and the second extract to obtain the pharmaceutical composition.

Preferably, the preparation method further comprises a step of: (4) extracting 3~14 parts by weight of a jujuba in 60~75% concentration of the ethanol solution to obtain a third extract, and adding the third extract into the pharmaceutical composition.

According to another aspect of the present invention, a preparation method of a pharmaceutical composition is provided. The preparation method comprises a step of: (1) mixing 3~10 parts by weight of a *ginseng* extract having 20~40% content of a ginsenoside with 0.2~0.8 part by weight of a glycyrrhizically related acid having 80~98% purity to obtain a pharmaceutical composition.

Preferably, the preparation method further comprises a step of: (2) compounding a β-cyclodextrin with a jujuba extract extracted from 0.05~0.2 part by weight of a jujuba and having 1% jujuba cyclic adenosine monophosphate (cAMP) to obtain a jujuba extract compound, and adding the jujuba extract compound into the pharmaceutical composition.

Concretely speaking, there are only 2 to 3 pharmaceuticals, the *ginseng*, liquorice and/or jujuba in the pharmaceutical composition of the present invention.

*Ginseng*: The *ginseng* contains adenylate cyclase (AC) for stimulating adenosine, and the phosphodiesterase inhibitor. Both of the adenylate cyclase and phosphodiesterase inhibitor have synergism and collectively increase the cAMP in the cells. The phenylalanine is promoted by the *ginseng* to increase the synthesis of dopamine (DA) and norepinephrine (NE) through the blood-brain barrier, and thus the concentrations of the dopamine and norepinephrine are increased.

Liquorice: The glycyrrhizic acid and glycyrrhetinic acid in liquorice are strong cAMP phosphodiesterase inhibitors. The cAMP degradation is decreased by inhibiting cAMP phosphodiesterase, and then the usage of cAMP in the central nervous system is increased.

Jujuba: The jujuba contains a large amount of cAMP-like materials. The extrinsic non-hydrated cAMP can be participated in the metastasis of cAMP in the body and be analogized the enzyme's function, and the cAMP in the cells is increased.

The *ginseng*, liquorice and jujuba in the pharmaceutical composition of the present invention are paired and acted collectively by stimulating the adenylate cyclase to increase the concentration of cAMP in brain cells, and by inhibiting the cAMP phosphodiesterase to decrease the degradation of cAMP and increase the usage of cAMP. The concentration and activity of the increased cAMP can increase the synthesis and release of neurotransmitters, such as norepinephrine, etc. (referring to *Volume One, Principles of Neurosciences* regarding the related description of the cAMP to the synthesis of catecholamine (CA)). This process is the mechanism of the modern pharmacology for anti-depression in this composition.

In other words, in order to accomplish the purpose of the present invention, the preferred parts by weight of compositions of the present invention are described as follows.

1. Composition 1: 4~18 parts by weight of the *ginseng* and 3~14 parts by weight of the liquorice.

The preferred composition of the medicine prepared by the raw materials of the weight ratio is described as follows: 9 parts by weight of the *ginseng* and 6 parts by weight of the liquorice.

2. Composition 2: 4~18 parts by weight of the *ginseng*, 3~14 parts by weight of the liquorice, and 3~14 parts by weight of the jujuba.

The preferred composition of the medicine prepared by the raw materials of the weight ratio is described as follows: 9 parts by weight of the *ginseng*, 6 parts by weight of the liquorice, and 6 parts by weight of the jujuba.

3. Composition 3: 3~10 parts by weight of the *ginseng* ethanol extract (containing 20~40% of the ginsenoside), 0.2~0.8 part by weight of the glycyrrhetinic acid (80~98% purity), and 0.05~0.2 part by weight of the jujuba ethanol extract (containing 0.5~3% of the jujuba cAMP).

In Composition 3, the preferred composition of the medicine prepared by the raw materials of the weight ratio is described as follows: 5 parts by weight of the *ginseng* ethanol extract (containing 30% of the ginsenoside), 0.4 part by weight of the glycyrrhetinic acid (90% purity), and 0.1 part by weight of the jujuba ethanol extract (containing 1% of the jujuba cAMP).

In order to prepare the pharmaceutical composition of the present invention, the pulverized substance of the *ginseng* and liquorice is directly used according to the dictated weight ratio of the composition, and the pharmaceutical composition is directly prepared. Another pharmaceutical composition is prepared by adding the jujuba dry powder on the basis of this pharmaceutical composition.

In addition, according to the component weight ratio of the composition, either a dry powder of the raw material is adopted, and the water extract or the ethanol extract of the other component is added to prepare the pharmaceutical composition of the present invention, or a water extract or an ethanol extract of the raw material is adopted, and the dry powder of the other component is added to prepare the pharmaceutical composition of the present invention.

The preparation method of the pharmaceutical composition of the present invention includes:

Method 1:

1. decocting 4~18 parts by weight of the *ginseng* in 60~77% concentration of the ethanol solution, separating and purifying by chromatography to obtain the first extract;

2. decocting 4~18 parts by weight of the liquorice in the water, concentrating and drying to obtain the second extract; and 3. mixing and sifting the first extract obtained from the step 1 and the second extract obtained from the step 2 to obtain the pharmaceutical composition 1 of the present invention.

The preferred composition of the medicine is 9 parts by weight of the *ginseng* and 6 parts by weight of the liquorice in the above method.

Method 2:

Three (3)~14 parts by weight of the jujuba (the preferred composition of the medicine is 6 parts by weight) is further added and decocted in the ethanol solution in Method 1, is then separated and purified by chromatography, and is compounded with the β-cyclodextrin to obtain the jujuba extract compound. The jujuba extract compound is mixed and pulverized with the first extract and the second extract to obtain the pharmaceutical composition 2 of the present invention.

Method 3:

1. Compounding 0.05~0.2 part by weight of the jujuba extract containing 1% of the jujuba cAMP with the β-cyclodextrin to obtain the jujuba extract compound.

2. Mixing the jujuba extract compound, 0.2~0.8 part by weight of the glycyrrhetinic acid having 90% purity and 3~10 parts by weight of the *ginseng* extract having 30% purity to obtain the pharmaceutical Composition 3 of the present invention.

The preferred parts by weight of each composition in the above method are: 0.1 part by weight of the jujuba extract having 1% of the jujuba cAMP (compounded with 9 parts by weight of the β-cyclodextrin), 5 parts by weight of the *ginseng* extract having 30% of the ginsenoside, and 0.4 part by weight of the glycyrrhetinic acid having 90% purity.

The resolving scheme of the herbal pharmaceutical composition of the present invention is to cooperate with the treating mechanism of modern medicine and pharmacology with regards to depression, so as to investigate and develop a herbal pharmaceutical composition for the treatment of depression as the main goal based on the principles of Chinese medicine. The characteristics are that all the raw materials are pharmaceutical that doubles as food, the combinations of pharmaceuticals are simple (only 2~3 pharmaceuticals), the function and mechanism are definite (conforming with the function and mechanism of modern pharmacology), the effects and ingredients can be quantified, and the curative effect is significant and safe. This kind of plant derived pharmaceuticals that doubles as food has no toxicity or side effects. It can be used as pharmaceuticals or health food for treating depression and be taken on a long term basis.

The pharmaceutical composition of the present invention can be administrated as the unit dose formula, and the way of administration can be intestinal or non-intestinal, such as oral administration, etc. The media include tablet, capsule, pill, roll, powder, solution, suspension, emulsion, and particle, etc. It can be prepared as immediate release, sustained release, controlled release, and microsphere delivery system. In order to prepare the unit delivery in tablet form, each carrier for one skilled in the art can be widely used. The examples regarding to the carriers are the dilutents and the absorbents, i.e. starch, dextrin, calcium sulphate, lactose, mannitol, sucrose, sodium chloride, glucose, urea, calcium carbonate, kaolin, microcrystalline cellulose, and aluminum silicate, etc. The further examples regarding to the carriers are the wetting agents and the bonding agents, i.e. water, glycerol, polyethylene glycol, ethanol, propanol, starch slurry, dextrin, syrup, honey, glucose solution, arabic mucilage, gelatin, sodium carboxymethylcellulose, lac, methyl cellulose, potassium phosphate, and poly vinyl pyrrolidone, etc. The further examples regarding to the carriers are the lysis agents, i.e. dried starch, alginate, agar, laminaran, sodium hydrogencarbonate, citric acid, calcium carbonate, polyoxyethylenesorbitanalkylester, sodium dodecyl-sulfonate, methyl cellulose, and ethyl cellulose, etc. The further examples regarding to the carriers are the lysis inhibitors, i.e. sucrose, tristearyl glycerol, cocoa butter, and hydrogenated oil, etc. The further examples regarding to the carriers are the absorbefacients, i.e. quaternary ammonium salt, and sodium dodecyl-sulfonate, etc. The further examples regarding to the carriers are the lubricants, i.e. talcum powder, silicon dioxide, corn starch, stearate, boric acid, liquid paraffin, and polyethylene glycol, etc. The tablet is further produced as the coating tablet, i.e. sugar coating tablet, film coating tablet, intestine-dissolving coating tablet, bi-layer tablet, and multi-layer tablet. In order to prepare the unit delivery in Chinese medicine pill form, each carrier for one skilled in the art can be widely used. The examples regarding to the carrier are the dilutents and the absorbents, i.e. glucose, sucrose, starch, cocoa butter, hydrogenated vegetable oil, poly vinyl pyrrolidone, Gelucire, kaolin, talcum powder, etc. The further examples regarding to the carrier are the bonding agents, i.e. arabic gum, tragacanth gum, gelatin, ethanol, honey, liquid sugar, rice slurry, and batter, etc. The further examples regarding to the carrier are the lysis agents, i.e. agar, dried starch, alginate, sodium dodecyl-sulfonate, methyl cellulose, and ethyl cellulose, etc. In order to prepare the unit delivery in suppository form, each carrier for one skilled in the art can be widely used. The examples regarding to the carrier are polyethylene glycol, lecithin, cocoa butter, high alcohol, high alcohol ester, gelatin, semi-synthetic glyceride, etc. In order to prepare the unit delivery in capsule form, the pharmaceutical composition or the extract of the present invention are mixed with each carrier described above, and the mixtures obtained from these methods are added into the hard gelatin capsules or the soft capsules. The pharmaceutical composition and the extract of the present invention can be prepared as the microcapsule, and be suspended in aqueous medium to form the suspension. This can be applied to be added into hard capsules.

Furthermore, if necessary, coloring agents, spices, flavor enhancers, sweeteners, and other materials can be added into the pharmaceutical composition.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiment 1

Figure 1:
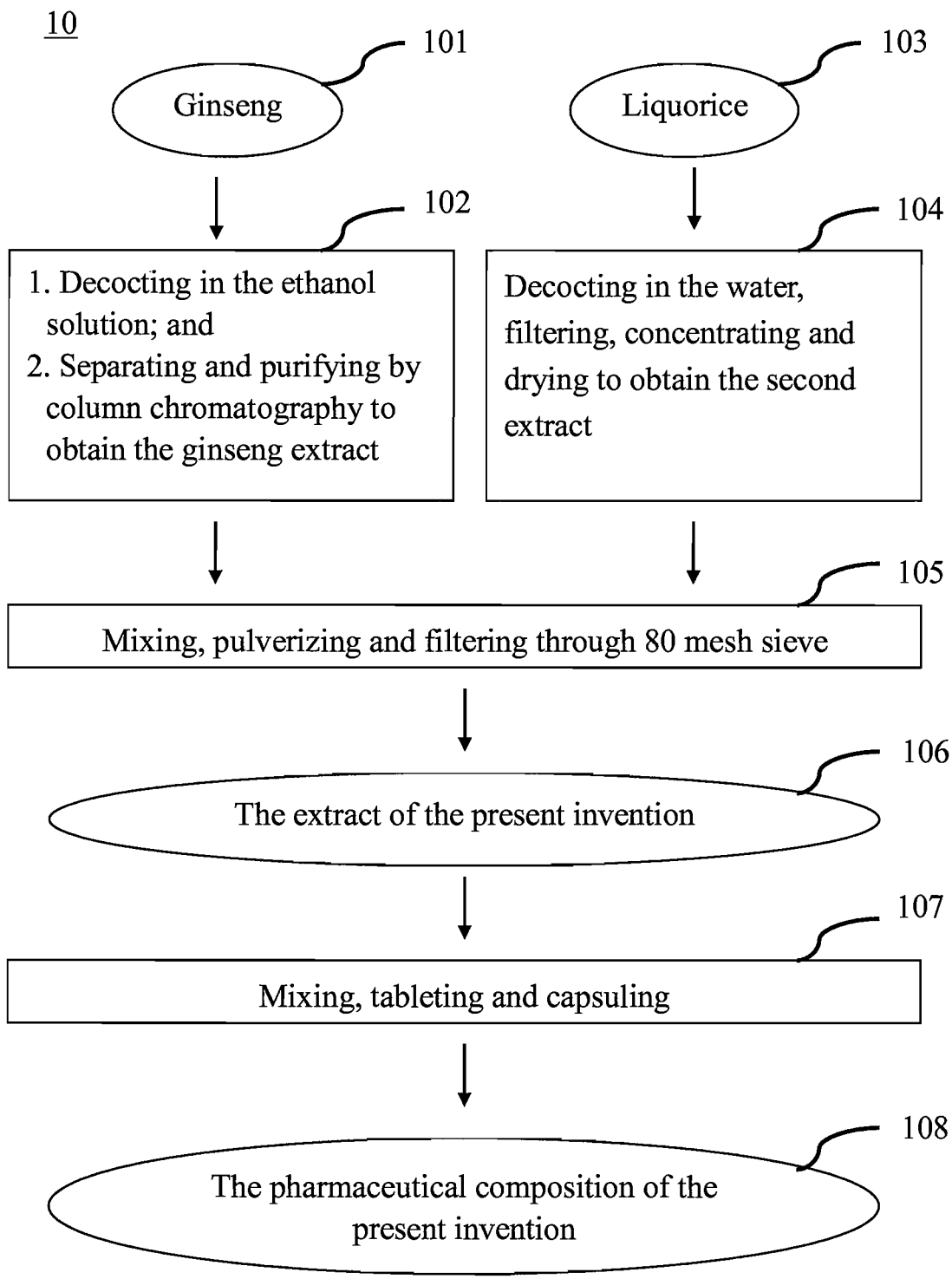
FIG. 1 is a flowchart diagram showing a preparation method of a pharmaceutical composition in accordance with a first preferred Embodiment of the present invention.

Please refer to FIG. 1, which is a flowchart diagram showing a preparation method of a pharmaceutical composition in accordance with a first preferred Embodiment of the present invention. FIG. 1 adopts the method which one is skilled in the art. Nine (9) kg of the *ginseng* (101) is decocted in ethanol solution of 75% purity, and then is separated and purified by column chromatography to obtain the first extract (102). The first extract has 40% of ginsenoside. Six (6) kg of the liquorice (103) is decocted in the water solution, and then filtered, concentrated, and dried to obtain the second extract (104). The first extract is mixed with the second extract, and then is pulverized to obtain the first pharmaceutical composition of the present invention (105, 106, 107, and 108).

Embodiment 2

Figure 2:
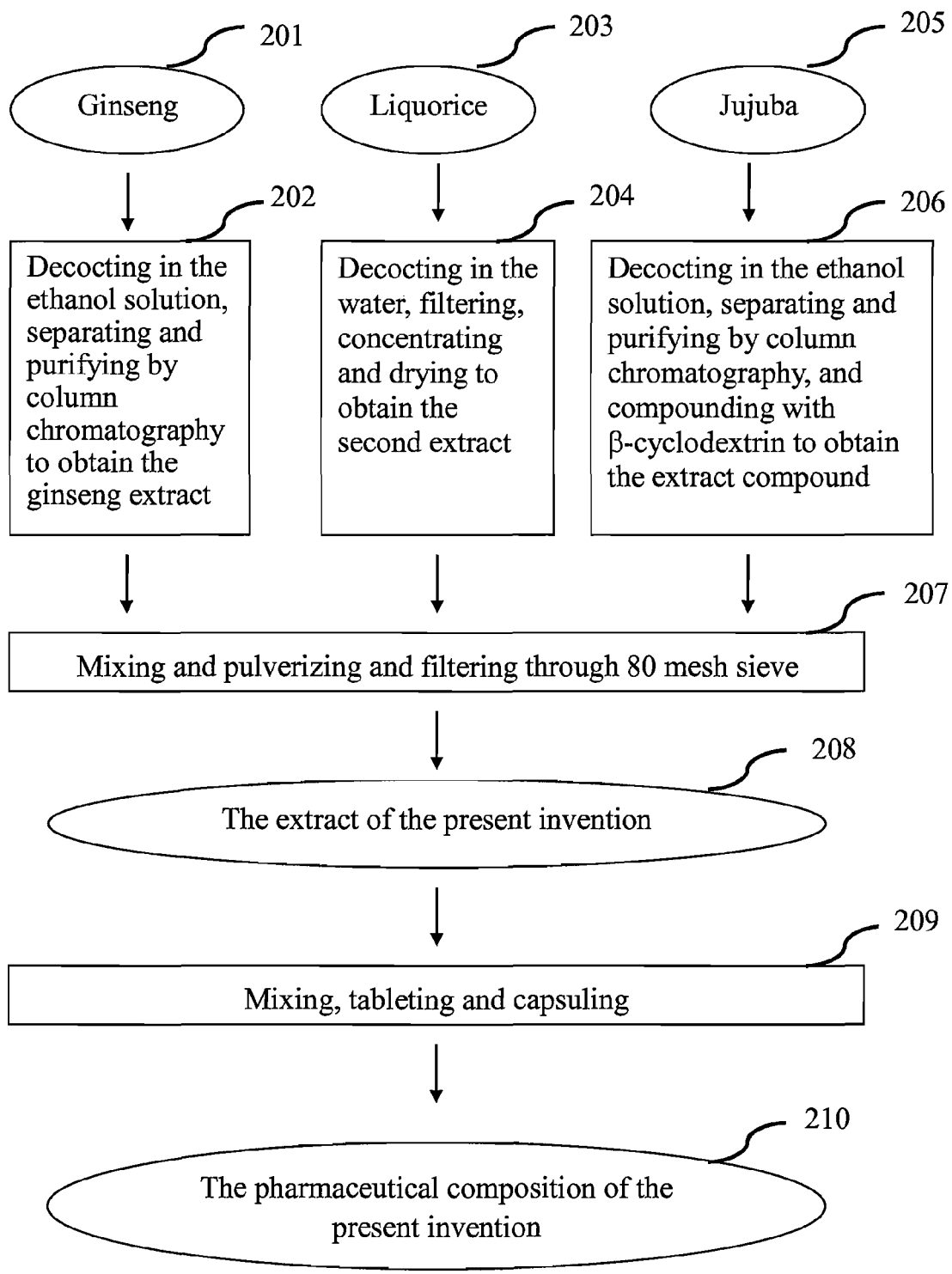
FIG. 2 is a flowchart diagram showing a preparation method of a pharmaceutical composition in accordance with a second preferred Embodiment of the present invention.

Please refer to FIG. 2, which is a flowchart diagram showing a preparation method of a pharmaceutical composition in accordance with a second preferred Embodiment of the present invention. In FIG. 2, 9 kg of the *ginseng* (201) is decocted in 60% of ethanol solution, and then separated and purified by column chromatography to obtain the first extract (202). Six (6) kg of the liquorice (203) is decocted in water solution, and then filtered, concentrated, and dried to obtain the second extract (204). Six (6) kg of the jujuba (205) is decocted in 75% of ethanol solution, and then separated and purified by column chromatography to obtain the third extract. The third extract is compounded with 9 parts by weight of the β-cyclodextrin to obtain the extract compound (206). The first extract, the second extract, and the extract compound of the third extract are mixed and pulverized to obtain the second pharmaceutical composition of the present invention (207, 208, 209, and 210).

Embodiment 3

Figure 3:
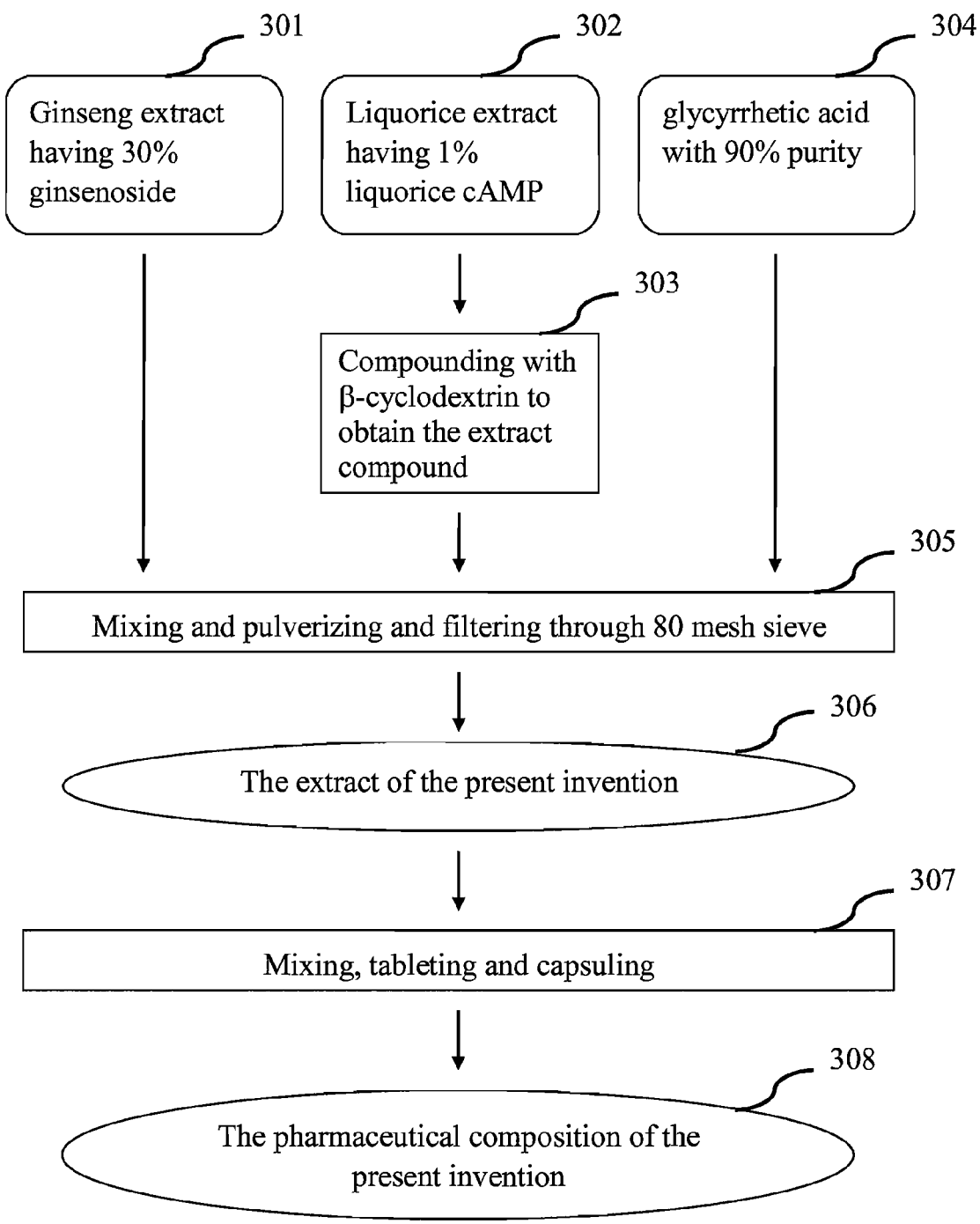
FIG. 3 is a flowchart diagram showing a preparation method of a pharmaceutical composition in accordance with a third preferred Embodiment of the present invention.

Please refer to FIG. 3, which is a flowchart diagram showing a preparation method of a pharmaceutical composition in accordance with a third preferred Embodiment of the present invention. One (1) g of the jujuba extract (having 1% of jujuba cAMP) (302) is compounded with 9 g of β-cyclodextrin to obtain 10 g of extract compound (303). Ten (10) g of extract compound, 50 g of *ginseng* extract (having 30% of ginsenoside) (301), and 4 g of glycyrrhetinic acid (90% purity) (304) are mixed and pulverized to obtain the third pharmaceutical composition of the present invention (305, 306, 307, and 308).

Embodiment 4

Four (4) kg of *ginseng* and 3 kg of liquorice are pulverized into dry powder. After the obtained dry powder is mixed by the preparation method adopted by one skilled in the art, the pharmaceutical bonding agent, such as honey, etc. is added to prepare the honey pills.

Embodiment 5

This pharmaceutical composition is prepared by adopting the same method that of Embodiment 4. The difference is adopting 18 kg of *ginseng* and 14 kg of liquorice.

Embodiment 6

Four (4) kg of commercial *ginseng* and 3 kg of liquorice are pulverized into dry powder. After the obtained dry powder is mixed by the preparation method adopted by one skilled in the art, 0.2 kg of jujuba ethanol extract and pharmaceutical carriers, i.e. starch and dextrin, are added to prepare the pills.

Embodiment 7

Eighteen (18) kg of the commercial *ginseng* water extract and 14 kg of the liquorice are pulverized into dry powder. After the obtained dry powder is mixed by the preparation method adopted by one skilled in the art, the pharmaceutical carriers, i.e. starch and dextrin, are added to prepare the pills.

Embodiment 8

Four (4) kg of *ginseng* and 14 kg of liquorice water extract obtained by the method of Embodiment 1 (10) are pulverized into dry powder. After the obtained dry powder is mixed by the preparation method adopted by one skilled in the art, then 14 kg of 70% of jujuba water extract obtained by the method of the Embodiment 2 (20), and the pharmaceutical carriers, i.e. starch and dextrin, are added to prepare the pills.

Embodiment 9

After 3 kg of the commercial *ginseng* ethanol extract having 40% of ginsenoside and 0.2 kg of glycyrrhetinic acid are mixed to obtain a mixture, the pharmaceutical pills are prepared by the method adopted by one skilled in the art.

Embodiment 10

After 4 kg of the commercial *ginseng* ethanol extract containing 20% of ginsenoside and 0.8 kg of glycyrrhizic acid are mixed to obtain a mixture, the pharmaceutical soft capsules are prepared by the method adopted by person skilled in the art.

EXPERIMENT The Anti-Depression Experiment of the Present Invention

Experiment 1: "Mouse Tail-Hanging" Experiment

Experimental animal: ICR mice

Experimental pharmaceuticals: The pharmaceutical of the Embodiment 3 of the present invention is provided by Beijing Wonner Biotech Ltd. Co., the depression-relieving pill is the product of Zhengzhou Yumi Medicines Co. Ltd., and Paroxitine (Paxil) is the product of Zhong Mei Tianjin Smith Kline pharmaceuticals Co. Ltd.

Experimental Method:

I. Group division: 1. Large dose of the Embodiment 3 medicine of the present invention (188.5 mg/kg), 2. middle dose of the Embodiment 3 medicine of the present invention (94.25 mg/kg), 3. small dose of the Embodiment 3 medicine of the present invention (47.125 mg/kg), 4. depression-reliving pill (650 mg/kg), 5. Paroxitine (16.7 mg/kg), and 6. physiological saline. (Ten (10) mice are in each group.)

II. Administration of drug: The abovementioned pharmaceutical water solutions are fed into the stomach according to 0.2 ml/10 g body weight, 2 times per day for a total of 7 days. After 1 hour of the last administration of drug, the mouse tail-hanging experiment is proceeded.

III. Mouse tail-hanging experiment: The mouse's tail (near to the tail end for 1 cm) is taped on the 5 cm of the wood strip of the high mountain platform and hanged up for 6 minutes. The time of non-movement of the mouse for the last 5 minutes is recorded.

Experimental Result:

The variance analysis calculation and the p-value compared with the control of the experimental result are calculated by using SPSS 11.5 analytic software.

| Group | Animal number | Time of non-movement (s) | p-value |
|---|---|---|---|
| Physiological saline (control) | 10 | 122.66 ± 33.53 | |
| Depression-reliving pill | 10 | 88.21 ± 52.50 | 0.081 |
| Paroxitine | 10 | 54.98 ± 46.92 | 0.01 |
| Large dose of the Embodiment 3 medicine of the present invention | 10 | 60.41 ± 36.42 | 0.02 |
| Middle dose of the Embodiment 3 medicine of the present invention | 10 | 72.68 ± 55.37 | 0.013 |
| Small dose of the Embodiment 3 medicine of the present invention | 10 | 84.35 ± 27.56 | 0.053 |

Conclusion: According to the above experiment, it is shown that the time of non-movement after the mouse tail-hanging experiment is decreased in all of the large, middle and small doses of the Embodiment 3 medicine of the present invention, and has significant difference compared with the physiological saline (control). Therefore, the Embodiment 3 of the present invention is inferred to have anti-depression function.

Experiment 2: Body Temperature Decrease Experiment Induced by Resetpine

Experimental animal: ICR mice

Experimental pharmaceuticals: The pharmaceutical of the Embodiment 3 of the present invention is provided by Beijing Wonner Biotech Ltd. Co., the depression-relieving pill is the product of Zhengzhou Yumi Medicines Co. Ltd., and Paroxitine (Paxil) is the product of Zhong Mei Tianjin Smith Kline pharmaceuticals Co. Ltd.

Experimental Method:

I. Group division: 1. Large dose of the Embodiment 3 medicine of the present invention (188.5 mg/kg), 2. middle dose of the Embodiment 3 medicine of the present invention (94.25 mg/kg), 3. small dose of the Embodiment 3 medicine of the present invention (47.125 mg/kg), 4. depression-reliving pill (650 mg/kg), 5. Paroxitine (16.7 mg/kg), and 6. physiological saline. (Ten (10) mice are in each group.)

II. Administration of drug: the abovementioned pharmaceutical water solutions are fed into the stomach according to 0.2 ml/10 g body weight, 2 times per day for a total of 7 days.

III. After the last administration of drug, the anal temperature (abbreviated as anal temp.) is determined, and then 2 mg resetpine per kg of the body weight is taken by intraperitoneal injection. After injecting the resetpine for 2, 3, 4, 5, 6 and 7 hours respectively, the anal temperature of the mice are determined.

Experimental Result:

The variance analysis calculation and the p-value compared with the control of the experimental result are calculated by using SPSS 11.5 analytic software.

| Group | Animal number | Decreased anal temp. for 2 hr (° C.) | p-value | Decreased anal temp. for 3 hr (° C.) | p-value | Decreased anal temp. for 4 hr (° C.) | p-value |
|---|---|---|---|---|---|---|---|
| Physiological saline (control) | 10 | 2.63 ± 0.56 | | 2.33 ± 0.85 | | 2.84 ± 0.84 | |
| Paroxitine | 10 | 1.29 ± 0.47 | 0.001 | 1.08 ± 0.35 | 0.001 | 1.55 ± 0.64 | 0.001 |
| Depression-reliving pill | 10 | 2.03 ± 0.55 | 0.003 | 2.67 ± 0.48 | 0.201 | 2.88 ± 0.65 | 0.882 |
| Large dose of the Embodiment 3 medicine of the present invention | 10 | 1.82 ± 0.38 | 0.001 | 1.77 ± 0.51 | 0.038 | 2.92 ± 0.51 | 0.767 |
| Middle dose of the Embodiment 3 medicine of the present invention | 10 | 0.90 ± 0.44 | 0.001 | 0.48 ± 0.36 | 0.001 | 0.85 ± 0.21 | 0.001 |
| Small dose of the Embodiment 3 medicine of the present invention | 10 | 2.63 ± 0.43 | 0.815 | 2.04 ± 0.77 | 0.275 | 1.45 ± 0.55 | 0.001 |

| Group | Animal number | Decreased anal temp. for 5 hr (° C.) | p-value | Decreased anal temp. for 6 hr (° C.) | p-value | Decreased anal temp. for 7 hr (° C.) | p-value |
|---|---|---|---|---|---|---|---|
| Physiological saline (control) | 10 | 2.97 ± 0.51 | | 2.60 ± 0.57 | | 3.05 ± 0.67 | |
| Paroxitine | 10 | 1.44 ± 0.32 | 0.001 | 2.51 ± 0.47 | 0.720 | 2.76 ± 0.59 | 0.272 |
| Depression-reliving pill | 10 | 2.49 ± 0.60 | 0.033 | 2.71 ± 0.46 | 0.660 | 3.45 ± 0.65 | 0.131 |
| Large dose of the Embodiment 3 medicine of the present invention | 10 | 2.88 ± 0.44 | 0.683 | 2.43 ± 0.64 | 0.499 | 2.30 ± 0.57 | 0.006 |
| Middle dose of the Embodiment 3 medicine of the present invention | 10 | 1.29 ± 0.56 | 0.001 | 1.08 ± 0.59 | 0.001 | 1.08 ± 0.39 | 0.001 |
| Small dose of the Embodiment 3 medicine of the present invention | 10 | 2.28 ± 0.48 | 0.003 | 2.68 ± 0.61 | 0.750 | 2.29 ± 0.59 | 0.005 |

Conclusion: According to the above results, it is shown that all of the large, middle, and small doses of the Embodiment 3 of the present invention have the function against the decrease of the mice anal temperature induced by resetpine. The middle dose has significant difference compared with the physiological saline (control). Therefore, the Embodiment 3 of the present invention is inferred to have anti-depression function.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for treating depression in a patient in need thereof, the method comprising administering to the patient an effective amount of a pharmaceutical composition comprising:
- an ethanolic *ginseng* extract extracted from 4~6 parts by weight of *ginseng*, wherein the *ginseng* extract has a ginsenoside content of 25~35%; and
- 0.3~0.5 parts by weight of glycyyrhizic acid and/or glycyrrhizic acid.

2. The method according to claim 1, wherein the pharmaceutical composition further comprises an ethanolic jujuba extract extracted from 0.00025~0.6 part by weight of a jujuba, wherein the jujuba extract has a jujuba cyclic adenosine monophosphate (cAMP) of 0.5~3%.

3. The method according to claim 2, wherein the ethanolic jujuba extract is extracted from 0.8~0.12% part by weight of a jujuba, and has a purity of jujuba cAMP of 0.8~1.2%.

4. The method according to claim 1, wherein the pharmaceutical composition further comprises a pharmacologically acceptable additive.

5. The method according to claim 1, wherein the pharmaceutical composition is selected from a group consisting of a powder, a capsule, a tablet, and a pill.

6. A method for treating depression in a patient in need thereof, the method comprising administering to the patient an effective amount of a pharmaceutical composition comprising:
- an ethanolic *ginseng* extract extracted from 4~6 parts by weight of *ginseng*, wherein the *ginseng* extract has a ginsenoside content of 25~35%;
- 0.3~0.5 parts by weight of glycyyrhizic acid and/or glycyrrhizic acid; and
- an ethanolic jujuba extract extracted from 0.00025~0.6 part by weight of a jujuba.

7. The method according to claim 6, wherein the pharmaceutical composition further comprises a pharmacologically acceptable additive.

8. The method according to claim 6, wherein the pharmaceutical composition is selected from a group consisting of a powder, a capsule, a tablet, and a pill.

* * * * *